United States Patent
Hakky

Patent Number: 6,159,209
Date of Patent: Dec. 12, 2000

[54] AUTOMATIC RESECTOSCOPE

[75] Inventor: Said I. Hakky, Largo, Fla.

[73] Assignee: Canox International Ltd., Largo, Fla.

[21] Appl. No.: 09/271,590

[22] Filed: Mar. 18, 1999

[51] Int. Cl.$^7$ .................................................. A61B 17/32
[52] U.S. Cl. ............................ 606/45; 606/46; 606/170; 606/180; 604/22
[58] Field of Search ................... 606/41, 45, 46, 606/49, 50, 169, 170, 171, 180; 604/22

[56] References Cited

U.S. PATENT DOCUMENTS

| | | | |
|---|---|---|---|
| 5,133,713 | 7/1992 | Huang et al. | 606/46 |
| 5,810,809 | 9/1998 | Rydell | 606/49 |
| 5,904,681 | 5/1999 | West, Jr. | 606/41 |
| 5,913,857 | 6/1999 | Richart et al. | 606/45 |
| 5,941,876 | 8/1999 | Nardella et al. | 606/45 |
| 6,007,533 | 12/1999 | Casscells et al. | 606/45 |
| 6,032,673 | 3/2000 | Savage et al. | 606/46 |

*Primary Examiner*—Linda C. M. Dvorak
*Assistant Examiner*—David M. Ruddy
*Attorney, Agent, or Firm*—Rosenberg, Klein & Lee

[57] ABSTRACT

A device for coagulating, vaporizing, resecting, and removing prostate and bladder tissue. The resectoscope uses the standard diathermy electrical units available at hospitals. The resectoscope uses a rotating cutting/coagulation element to cut, coagulate and vaporize tissue at a much higher speed compared to the linear motion of currently available resectoscopes, allowing the operator to perform these procedures more efficiently, and also allowing the operator to retrieve most of the excised tissue for histological examinations.

2 Claims, 3 Drawing Sheets

AUTOMATIC RESECTOSCOPE

BACKGROUND OF THE INVENTION

1. Field of the Invention

The present invention relates generally to a surgical device, and, in particular, to a resectoscope having electrically powered cutting and coagulating/vaporizing means for cutting, coagulating, and removing tissue from a patient during a surgical procedure.

2. Description of the Prior Art

A resectoscope is employed transurethrally to perform bladder and/or prostate surgery. This device generally contains an elongated section provided with an outer sheath made of stainless steel which is inserted into the urethra. This outer sheath prevents the urethra from contracting, while the working elements of the device are located within the sheath. These working elements are employed to cut, coagulate, vaporize and retrieve the target tissue.

Conventional resectoscopes are manually operated; a heated cutting/coagulating element, known as a diathermy wire loop, is extended manually beyond the end of the outer sheath to a position engaging the tissue to be cut. The cutting element is then energized through activation of a diathermy unit connected to the resectoscope, and at the same time the cutting element is manually retracted, slicing away a section of prostate or bladder tissue. The surgeon must view the surgical site through a telescopic system which is also contained within the working element. In addition, it is necessary to continuously irrigate the surgical site to keep the viewing area free of blood and tissue debris for the surgeon.

During typical prostate surgery, it is common to excise approximately 0.1 gram of tissue with each cutting stroke. Although the total weight of the tissue to be removed varies with the size of the prostate, it is quite common to remove anywhere from 20 to 60 grams of prostate tissue in a typical transurethral resection of the prostate. Thus, in a standard procedure, it is necessary to manually reciprocate the cutting element at least 200 times, which is quite time consuming and could possibly affect the morbidity of the operation result.

U.S. Pat. No. 4,657,018, which issued to Hakky, discloses a resectoscope capable of automatic operation; the surgeon can perform the prostate or bladder procedure either manually or automatically. This automatic/manual resectoscope uses a linear cutting approach, which has several inherent drawbacks. For example, the operating speed is limited, which reduces one of the advantages offered by this device, and certain areas of the prostate anatomy cannot be easily accessed by linear motion.

This problem is addressed in U.S. Pat. Nos. 4,955,882; 5,201,731; and 5,498,258, which all teach rotary techniques in cutting and retrieving resected prostate or bladder tissue. In addition, U.S. Pat. No. 5,498,258 teaches the use of TEFLON coated rotary blades which are heated by a laser to cut and coagulate prostate or bladder tissue.

In certain parts of the world a laser unit may not be readily available in the operating room; there is, however, a diathermy unit located in every operating room worldwide. It is possible to substitute this unit for a laser, and by combining diathermy with a rotary cutting mechanism a more efficient procedure can be performed, which will be reflected in the quicker recovery of the patient. The procedure can now be performed on an outpatient basis with minimal anesthesia.

SUMMARY OF THE INVENTION

It is therefore an object of the present invention to automatically cut and coagulate the prostate or bladder tissue using the electric diathermy unit in a reliable and efficient manner.

It is a further object of the present invention to provide a resectoscope which can operate in a rotating movement powered by a motor, thus increasing the speed, efficiency, and safety while decreasing the cost of endoscopic surgery of the bladder and the prostate.

It is still a further object of the present invention to provide an apparatus to retrieve the cut or coagulated tissue for pathological examination.

It is still a further object of the present invention to provide an electric resectoscope for cutting, coagulating, and vaporizing of tissue.

It is a further object of the present invention to provide a continuous irrigation and suction for removal of resected tissue for pathological examination.

It is yet a further object of the present invention to provide a rotating cutting/coagulating member which can easily interchange with different kinds of cutting/coagulation devices.

These and other objects and advantages of the present invention will be more readily apparent in the description which follows.

DETAILED DESCRIPTION OF THE PREFERRED EMBODIMENT

Figure 1:
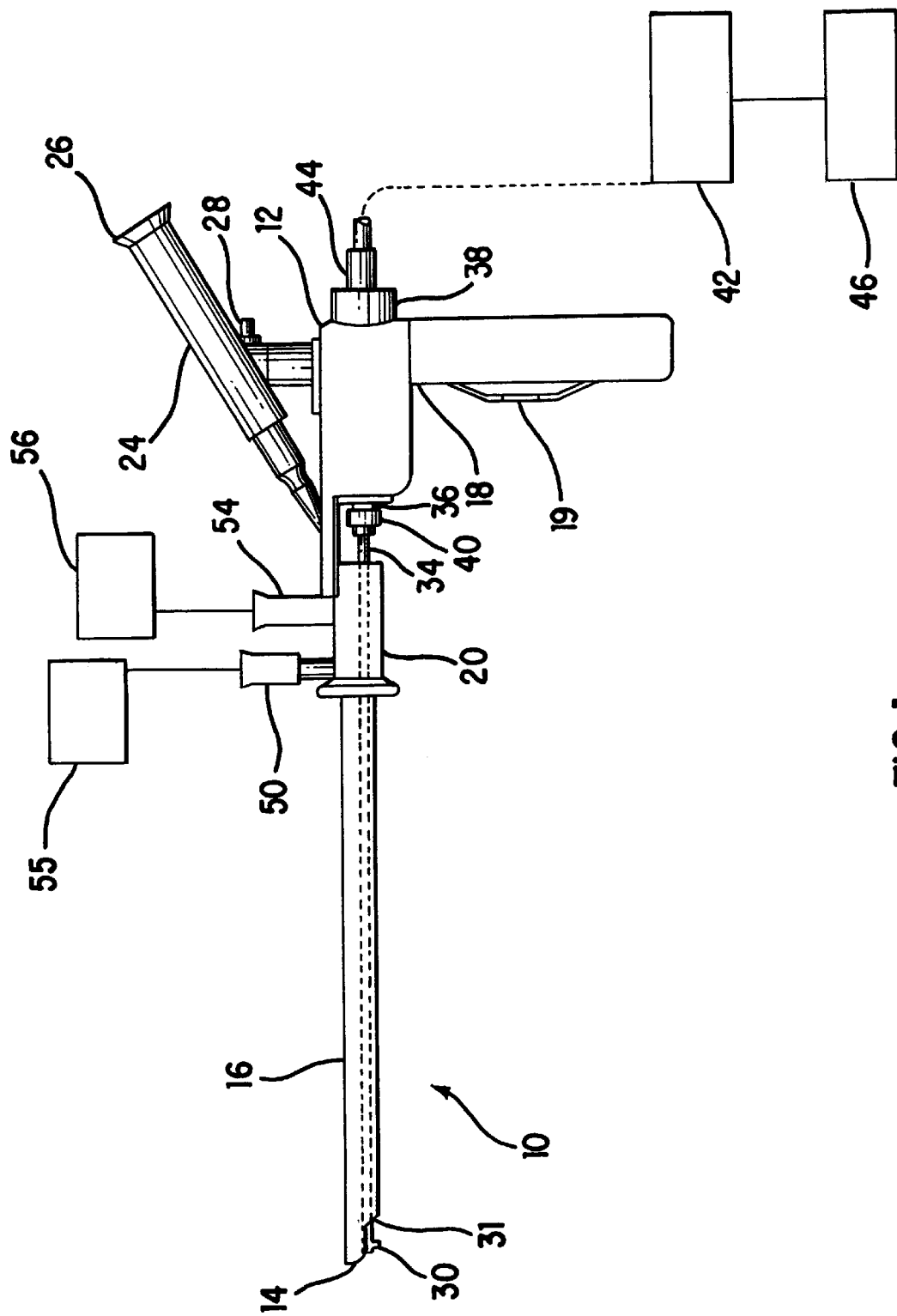
FIG. 1 is a side elevational view of the resectoscope of the present invention.

Referring more particularly to the drawings, there is shown in FIG. 1 a resectoscope, generally indicated at 10, which embodies the principles of the present invention. Resectoscope 10, which has a proximal end 12 and a distal end 14, contains an elongated hollow cylindrical sheath 16 adapted to be inserted at distal end 14 into the urethra of a patient for the purpose of performing prostate or bladder surgery. Sheath 16 is affixed near proximal end 12 to a handle 18, having an activating switch 19, by a coupling 20.

An optical fiber 22 is located within sheath 16, and extends from distal end 14 to an image viewing means 24 located at proximal end 12 and attached to handle 18. Viewing means 24 includes an eyepiece 26 and a side opening 28 through which a light source is coupled. Image viewing means 24 preferably includes prisms and lenses which illuminate the surgical site and allow the surgeon to visualize a thirty degree angle view of the procedure looking through eyepiece 26.

Figure 2:
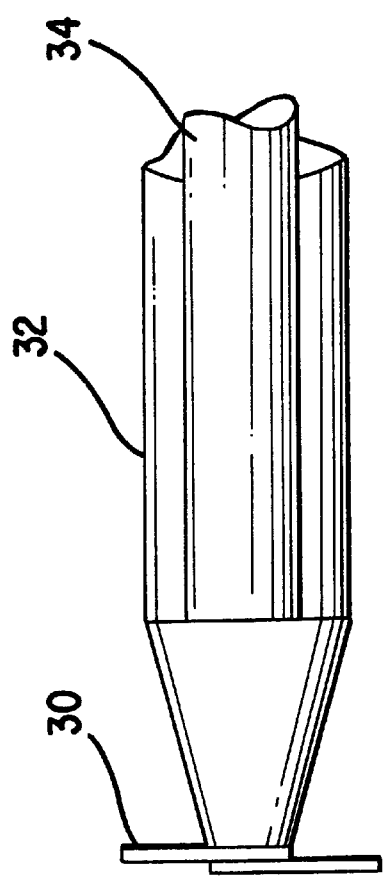
FIG. 2 is an enlarged view of the cutting mechanism of the resectoscope of FIG. 1.

A rotating cutting/coagulating means 30 is positioned at distal end 14 extending below a cutaway section 31 of sheath 16. Rotary cutter 30, which preferably is constructed as a removable unit 32, as shown in FIG. 2, is rigidly coupled to a rod 34 which extends through sheath 16 and is coupled to a shaft 36 of a rotary motor 38 (located within handle 18) by a coupler 40. An electric diathermy unit 42 is coupled to rod 34 via a connector 44 located at proximal end 12 of handle 18 such that rod 34 conducts current for coagulating purposes. Thus, rod 34 and removable unit 32 must be insulated to prevent electric shock. A control means 46 is coupled to unit 42 to allow the surgeon to selectively operate the cutting and coagulating modes of resectoscope 10. Control means 46 is preferably a foot pedal which gives the surgeon hands-free control of the selection.

A upper fluid conduit 48 extends within sheath 16 from distal end 14 through coupling 20 to an inlet port 50, while a lower fluid conduit 52 also extends within sheath 16 from distal end 14 through coupling 20 to an outlet port 54. An irrigating fluid from a fluid reservoir 55 is introduced into inlet port 50 and is delivered to the operation site via conduit: 48 as shown by arrows A. This fluid, which is mixed with blood, resected tissue, and debris is carried away from the site as shown by arrows B through conduit 52 and out through port 54 by means of a suction device 56 which is coupled to port 54.

Having described the elements of the device of the present invention, the operation of the preferred embodiment of resectoscope 10 will now be described. After lubricating sheath 16 liberally, distal end 14 is inserted urethrally to the prostate area or bladder as desired by the surgeon. An irrigating fluid, preferably glycine, is introduced into port 50 and conduit 48 to the operating site. It should be noted that saline cannot be used as an irrigating fluid with this instrument, as the electric current at cutting device 30 will polarize the fluid into Na and Cl ions. The surgeon, while holding resectoscope 10 by handle 18, activates the device by activating switch 19 when it is in the proper operating position. This activation causes shaft 36 of motor 38, coupler 40, rod 34, and cutting device 30 to rotate. In the present embodiment, the rotary speed of cutter 30 is controlled by the amount of force applied by the surgeon to switch 19.

Figure 3:
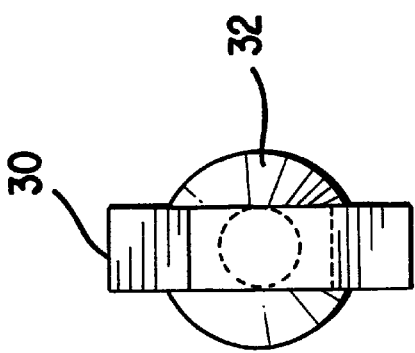
FIG. 3 is an end view of the cutting mechanism of FIG. 2.
Figure 5:
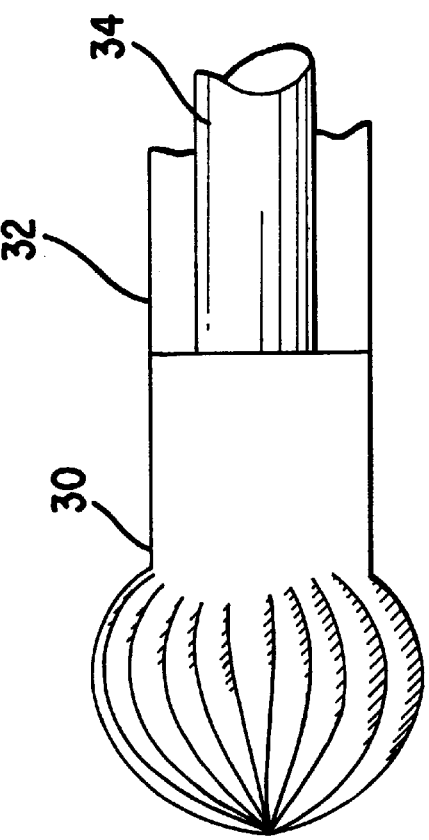
FIG. 5 is an enlarged view of an alternative cutting mechanism for use with the resectoscope of the present invention.
Figure 4:
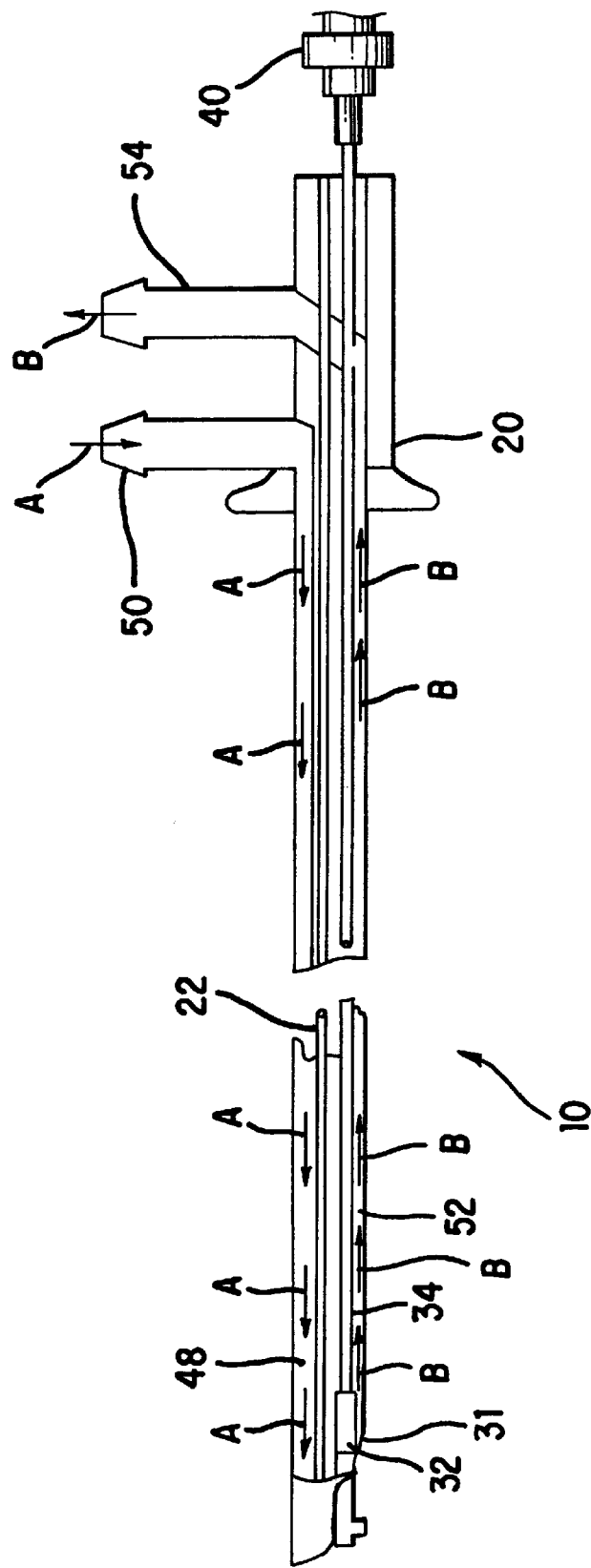
FIG. 4 is a fragmentary cross-sectional view of the resectoscope of FIG. 1.

Cutting device 30 may be constructed in many different configurations, depending on the type and complexity of the surgical procedure. Cutter 30 can be in the shape of a sharp blade, as shown in FIGS. 2 and 3, or may be provided with multiple cutting surfaces, as shown in FIG. 5. As cutter 30 is manufactured as removable unit 32, the surgeon can easily select the proper cutting/coagulating configuration for the surgical procedure he is performing. For example, in certain bladder procedures where the precise depth of tissue incision is important, a shallow multiple cutter would be used. Or in a prostate resection, where a large piece of tissue is to be removed, a sharp blade is selected. All of cutters 30 are constructed from stainless steel with TEFLON coated blades to prevent tissue adherence to the cutting edges, since if tissue builds up on cutter 30, it would be impossible or very difficult to coagulate the bleeding points, as electrical contact would be very poor for diathermy control.

The surgeon can control the amount of cutting/coagulation of the tissue by control means 46. Controller 46, which in the present embodiment comprises a foot switch, has a cutting current switch and a coagulating current switch. In areas where more precise cutting/coagulation is needed, the speed of rotation is kept to a minimum using switch 19. Or, if brisk bleeding is visualized, cutter 30 is slowed to a minimum speed via switch 19 and coagulating is performed by controller 46 to coagulate the desired tissue to stop the severe bleeding.

The resected tissue with blood will be aspirated along through conduit 52 and out of port 54 to suction device 56, where the resected tissue can be removed and examined.

The entire surgical procedure, using the device of the present invention, is performed faster and more precisely; thus, less anesthesia and irrigation fluid is absorbed into the vascular system. For example, when cutter 30 rotates at a speed of 2000 to 10,000 rpm, a 50 gram prostate will be removed in less than 5 minutes, as the number of grams which can be removed by the present device can range from 10 to 15 grams per minute. Thus, a typical 20 to 50 gram prostate operation which typically takes 20 to 50 minutes, will be reduced to less than 5 minutes with the present invention, allowing the patient to be discharged within a few hours of the procedure.

The resectoscope of the present invention is arranged to conduct the removal of internally located tissue from a patient quickly, easily, and with little or no bleeding using a rotating cutter/coagulating means. Moreover, the resectoscope is constructed such that the tissue removed is suitable for histological examination, since the cellular structure is substantially preserved.

While the present invention has been shown and described in terms of a preferred embodiment thereof, it will be understood that this invention is not limited to this particular embodiment and that many changes and modifications may be made without departing from the true spirit and scope of the invention as defined in the appended claims. In addition, as used herein and in the claims, such words as "distal", "proximal", "top", "bottom", "side", and the like are used in conjunction with the drawings for purposes of clarity, and it will be appreciated that they do not limit the device to a particular orientation.

What is claimed is:

1. A surgical apparatus for cutting and coagulating tissue from a patient during a surgical procedure, comprising:

an elongated hollow cylindrical member having a longitudinal axis including a proximal end portion and a distal end portion;

cutting means, positioned at said distal end of said cylindrical member, for cutting tissue at a surgical site;

a longitudinally extended first lumen disposed in said cylindrical member, said first lumen having an inlet coupled to an irrigation fluid source and an outlet opening adjacent said distal end of said cylindrical member for supplying irrigation fluid in proximity to said cutting means;

a longitudinally extended second lumen disposed in said cylindrical member, said second lumen having an inlet opening disposed adjacent said distal end of said cylindrical member and an outlet coupled to a suction source for removing said irrigation fluid, blood and debris from a region of the surgical site, said inlet opening of said second lumen being spaced proximally from said outlet opening of said first lumen;

an electrical power source;

rotatable motor means for operating said cutting means;

a current conducting shaft located within said cylindrical member and coupling said motor means to said cutting means to impart rotation to said cutting means, said shaft being electrically coupled to said power source for supplying electrical current to said cutting means for cutting and coagulating tissue; and, operating mode control means coupled to said power source for selectively supplying an electrical current level to said cutting means from said power source adapted for cutting or coagulating tissue.

2. The apparatus of claim 1, wherein said cutting means includes a cutter having at least a pair of cutting blades removably coupled to said shaft.

\* \* \* \* \*